US 6,585,651 B2

(12) United States Patent
Nolte et al.

(10) Patent No.: US 6,585,651 B2
(45) Date of Patent: Jul. 1, 2003

(54) METHOD AND DEVICE FOR PERCUTANEOUS DETERMINATION OF POINTS ASSOCIATED WITH THE SURFACE OF AN ORGAN

(75) Inventors: Lutz Peter Nolte, Hünibach (CH); Marwan Sati, Mississauga (CA); J. Christopher Moulder, Sherman Oaks, CA (US); Michael Wentkowski, Wigoltingen (CH); José L. Scherrer, Oensingen (CH)

(73) Assignees: Synthes AG Chur (CH); Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/982,949

(22) Filed: Oct. 22, 2001

(65) Prior Publication Data

US 2002/0120192 A1 Aug. 29, 2002

Related U.S. Application Data

(63) Continuation of application No. PCT/EP99/02634, filed on Apr. 20, 1999.

(51) Int. Cl.$^7$ ................................................. A61B 8/02
(52) U.S. Cl. ........................ 600/449; 600/437; 600/461; 600/407
(58) Field of Search ................................ 600/437–472, 600/407–409; 128/916

(56) References Cited

U.S. PATENT DOCUMENTS

| | | | |
|---|---|---|---|
| 3,821,469 A | 6/1974 | Whetstone et al. | 178/18 |
| 3,983,474 A | 9/1976 | Kuipers | 324/43 |
| 4,058,114 A | 11/1977 | Soldner | 128/2 |
| 4,146,924 A | 3/1979 | Birk et al. | 364/513 |
| 4,182,312 A | 1/1980 | Mushabac | 433/68 |
| 4,204,225 A | 5/1980 | Mistretta | 358/111 |
| 4,209,254 A | 6/1980 | Reymond et al. | 356/152 |
| 4,262,306 A | 4/1981 | Renner | 358/93 |
| 4,341,220 A | 7/1982 | Perry | 128/630 |
| 4,358,856 A | 11/1982 | Stivender et al. | 378/167 |
| 4,396,945 A * | 8/1983 | DiMatteo et al. | 600/438 |
| 4,418,422 A | 11/1983 | Richter et al. | 378/205 |
| 4,419,012 A | 12/1983 | Stephenson et al. | 356/141 |
| 4,437,161 A | 3/1984 | Anderson | 364/414 |
| 4,457,311 A | 7/1984 | Sorenson et al. | 128/660 |
| 4,465,069 A | 8/1984 | Barbier et al. | 128/303 |

(List continued on next page.)

FOREIGN PATENT DOCUMENTS

| | | |
|---|---|---|
| DE | 44 12 073 A1 | 4/1994 |
| DE | 195 06 197 A1 | 5/1996 |
| DE | 195 36 180 A1 | 6/1997 |

(List continued on next page.)

OTHER PUBLICATIONS

L–P Nolte, et al.; Clinical Evaluation of a System for Precision Enhancement in Spine Surgery, Clinical Biomechanics, vol. 10, No. 6, pp. 293–303, 1995.

Primary Examiner—Marvin M. Lateef
Assistant Examiner—William Jung
(74) Attorney, Agent, or Firm—Pennie & Edmonds LLP

(57) ABSTRACT

The present invention relates to a percutaneous-point determination device for determining a location of a point associated with a surface of an animal organ. The device comprises an ultrasound device configured to emit a focused ultrasound beam along an ultrasound beam axis having a known orientation with respect to the ultrasound device. The ultrasound device is configured to output ultrasound data indicative of a distance from the ultrasound device to the point. A position measurement device is configured to output position data indicative of a location of the ultrasound device. The device includes a computer configured to process the ultrasound data and position data to thereby determine a location of the point.

22 Claims, 1 Drawing Sheet

U.S. PATENT DOCUMENTS

| | | | |
|---|---|---|---|
| 4,473,074 A | 9/1984 | Vassiliadis | 128/303.1 |
| 4,485,815 A | 12/1984 | Amplatz et al. | 128/329 |
| 4,532,933 A * | 8/1985 | Hokanson | 348/139 |
| 4,543,959 A | 10/1985 | Seponen | 128/653 |
| 4,571,834 A | 2/1986 | Fraser et al. | 33/1 |
| 4,583,538 A | 4/1986 | Onik et al. | 128/303 |
| 4,592,352 A | 6/1986 | Patil | 128/303 |
| 4,598,368 A | 7/1986 | Umemura | 364/414 |
| 4,602,622 A | 7/1986 | Bär et al. | 128/303 |
| 4,613,866 A | 9/1986 | Blood | 343/448 |
| 4,613,942 A | 9/1986 | Chen | 364/513 |
| 4,618,978 A | 10/1986 | Cosman | 378/164 |
| 4,638,798 A | 1/1987 | Shelden et al. | 128/303 |
| 4,649,504 A | 3/1987 | Krouglicof et al. | 364/559 |
| 4,651,732 A | 3/1987 | Frederick | 128/303 |
| 4,670,781 A | 6/1987 | Aubert et al. | 358/93 |
| 4,672,564 A | 6/1987 | Egli et al. | 364/559 |
| 4,674,057 A | 6/1987 | Caughman et al. | 364/513 |
| 4,729,098 A | 3/1988 | Cline et al. | 364/414 |
| 4,733,661 A | 3/1988 | Palestrant | 128/303 |
| 4,733,969 A | 3/1988 | Case et al. | 356/375 |
| 4,737,032 A | 4/1988 | Addleman et al. | 356/376 |
| 4,742,815 A | 5/1988 | Ninan et al. | 128/4 |
| 4,743,770 A | 5/1988 | Lee | 250/560 |
| 4,743,771 A | 5/1988 | Sacks et al. | 250/560 |
| 4,745,290 A | 5/1988 | Frankel et al. | 250/360 |
| 4,750,487 A | 6/1988 | Zanetti | 128/303 |
| 4,753,528 A | 6/1988 | Hines et al. | 356/1 |
| 4,760,851 A | 8/1988 | Fraser et al. | 128/774 |
| 4,761,072 A | 8/1988 | Pryor | 356/1 |
| 4,762,016 A | 8/1988 | Stoughton et al. | 74/479 |
| 4,763,652 A | 8/1988 | Brisson et al. | 128/328 |
| 4,764,016 A | 8/1988 | Johansson | 356/371 |
| 4,776,749 A | 10/1988 | Wanzenberg et al. | 414/680 |
| 4,779,212 A | 10/1988 | Levy | 364/562 |
| 4,782,239 A | 11/1988 | Hirose et al. | 250/561 |
| 4,791,934 A | 12/1988 | Brunnett | 128/653 |
| 4,793,355 A | 12/1988 | Crum et al. | 128/653 |
| 4,794,262 A | 12/1988 | Sato et al. | 250/560 |
| 4,803,976 A | 2/1989 | Frigg et al. | 128/92 |
| 4,821,200 A | 4/1989 | Öberg | 364/474.24 |
| 4,821,206 A | 4/1989 | Arora | 364/513 |
| 4,822,163 A | 4/1989 | Schmidt | 356/1 |
| 4,825,091 A | 4/1989 | Breyer et al. | 250/560 |
| 4,829,373 A | 5/1989 | Leberl et al. | 358/88 |
| 4,835,710 A | 5/1989 | Schnelle et al. | 364/513 |
| 4,836,778 A | 6/1989 | Baumrind et al. | 433/69 |
| 4,841,967 A | 6/1989 | Chang et al. | 128/303 |
| 4,869,247 A | 9/1989 | Howard, III et al. | 128/303.1 |
| 4,875,478 A | 10/1989 | Chen | 128/303 |
| 4,896,673 A * | 1/1990 | Rose et al. | 356/141.4 |
| 4,907,252 A | 3/1990 | Aichinger et al. | 378/99 |
| 4,943,296 A | 7/1990 | Funakubo et al. | 606/166 |
| 4,945,914 A | 8/1990 | Allen | 128/653 |
| 4,955,891 A | 9/1990 | Carol | 606/130 |
| 4,970,666 A | 11/1990 | Welsh et al. | 364/522 |
| 4,987,488 A | 1/1991 | Berci | 358/93 |
| 4,991,579 A | 2/1991 | Allen | 128/563 |
| 5,016,639 A | 5/1991 | Allen | 128/653 |
| 5,027,818 A | 7/1991 | Bova et al. | 128/653 |
| 5,047,036 A | 9/1991 | Koutrouvelis | 606/130 |
| 5,050,608 A | 9/1991 | Watanabe et al. | 128/653 |
| 5,059,789 A | 10/1991 | Salcudean | 250/206.1 |
| 5,078,140 A | 1/1992 | Kwoh | 128/653.1 |
| 5,080,662 A | 1/1992 | Paul | 606/130 |
| 5,086,401 A | 2/1992 | Glassman et al. | 395/94 |
| 5,094,241 A | 3/1992 | Allen | 128/653.1 |
| 5,097,839 A | 3/1992 | Allen | 128/653.1 |
| 5,099,846 A | 3/1992 | Hardy | 128/653.1 |
| 5,107,839 A | 4/1992 | Houdek et al. | 128/653.1 |
| 5,119,817 A | 6/1992 | Allen | 128/653.1 |
| 5,142,930 A | 9/1992 | Allen et al. | 74/469 |
| 5,178,164 A | 1/1993 | Allen | 128/898 |
| 5,186,174 A | 2/1993 | Schlöndorff et al. | 128/653.1 |
| 5,197,476 A * | 3/1993 | Nowacki et al. | 356/141.4 |
| 5,198,877 A * | 3/1993 | Schulz | 356/141.4 |
| 5,207,223 A | 5/1993 | Adler | 128/653.1 |
| 5,211,164 A | 5/1993 | Allen | 128/653.1 |
| 5,211,165 A | 5/1993 | Dumoulin et al. | 128/653.1 |
| 5,230,338 A | 7/1993 | Allen et al. | 128/653 |
| 5,230,623 A | 7/1993 | Guthrie et al. | 433/72 |
| 5,249,581 A | 10/1993 | Horbal et al. | 128/664 |
| 5,251,127 A | 10/1993 | Raab | 364/413.13 |
| 5,257,998 A | 11/1993 | Ota et al. | 606/130 |
| 5,274,551 A | 12/1993 | Corby, Jr. | 364/413.13 |
| 5,278,756 A | 1/1994 | Lemchen et al. | 364/413.28 |
| 5,295,483 A | 3/1994 | Nowacki et al. | 128/660.03 |
| 5,299,288 A | 3/1994 | Glassman et al. | 395/80 |
| 5,300,080 A | 4/1994 | Clayman et al. | 606/130 |
| 5,305,203 A | 4/1994 | Raab | 364/413.13 |
| 5,309,913 A | 5/1994 | Kormos et al. | 128/653.1 |
| 5,325,855 A | 7/1994 | Daghighian et al. | 128/653.1 |
| 5,350,351 A | 9/1994 | Saffer | 601/2 |
| 5,383,454 A | 1/1995 | Bucholz | 128/653.1 |
| 5,389,101 A | 2/1995 | Heilbrun et al. | 606/130 |
| 5,394,457 A | 2/1995 | Leibinger et al. | 378/162 |
| 5,408,409 A | 4/1995 | Glassman et al. | 364/413.13 |
| 5,445,166 A | 8/1995 | Taylor | 128/897 |
| 5,477,736 A * | 12/1995 | Lorraine | 73/642 |
| 5,479,597 A | 12/1995 | Fellous | 395/154 |
| 5,483,961 A | 1/1996 | Kelly et al. | 128/653.1 |
| 5,494,034 A | 2/1996 | Schlöndorff et al. | 128/653.1 |
| 5,517,990 A | 5/1996 | Kalfas et al. | 128/653.1 |
| 5,383,454 A | 12/1996 | Bucholz | 128/653.1 |
| 5,588,430 A | 12/1996 | Bova et al. | 128/653.1 |
| 5,617,857 A | 4/1997 | Chader et al. | 128/653.1 |
| 5,622,170 A | 4/1997 | Schulz | 128/653.1 |
| 5,630,431 A | 5/1997 | Taylor | 128/897 |
| 5,631,973 A | 5/1997 | Green | 382/128 |
| 5,647,373 A * | 7/1997 | Paltieli | 600/567 |
| 5,662,111 A | 9/1997 | Cosman | 128/653.1 |
| 5,676,673 A | 10/1997 | Ferre et al. | 606/130 |
| 5,682,886 A | 11/1997 | Delp et al. | 128/653.1 |
| 5,711,299 A | 1/1998 | Manwaring et al. | 128/653.1 |
| 5,729,129 A | 3/1998 | Acker | 324/207.12 |
| 5,732,703 A | 3/1998 | Kalfas et al. | 128/653.2 |
| 5,735,278 A | 4/1998 | Hoult et al. | 128/653.2 |
| 5,748,767 A | 5/1998 | Raab | 382/128 |
| 5,755,725 A | 5/1998 | Druais | 606/130 |
| RE35,816 E | 6/1998 | Schulz | 356/376 |
| 5,769,078 A | 6/1998 | Kliegis | 128/653.1 |
| 5,769,789 A | 6/1998 | Wang et al. | 600/414 |
| 5,769,861 A | 6/1998 | Vilsmeier | 606/130 |
| 5,772,593 A | 6/1998 | Hakamata | 600/407 |
| 5,795,294 A | 8/1998 | Luber et al. | 600/407 |
| 5,799,099 A | 8/1998 | Wang et al. | 382/131 |
| 5,800,352 A | 9/1998 | Ferre et al. | 600/407 |
| 5,806,521 A * | 9/1998 | Morimoto et al. | 600/447 |
| 5,807,252 A | 9/1998 | Hassfeld et al. | 600/407 |
| 5,810,008 A * | 9/1998 | Dekel et al. | 600/443 |
| 5,829,444 A | 11/1998 | Ferre et al. | 128/897 |
| 5,848,967 A | 12/1998 | Cosman | 600/426 |
| 5,880,976 A | 3/1999 | DiGioia III et al. | 364/578 |
| 5,957,844 A * | 9/1999 | Dekel et al. | 600/349 |
| 5,995,738 A | 11/1999 | DiGioia, III et al. | 395/500.32 |
| 6,002,859 A | 12/1999 | DiGioia, III et al. | 395/500.32 |
| 6,021,343 A | 2/2000 | Foley et al. | 600/429 |
| 6,106,464 A * | 8/2000 | Bass et al. | |
| 6,112,113 A | 8/2000 | Van Der Brug et al. | 600/427 |
| 6,120,465 A | 9/2000 | Guthrie et al. | 600/587 |
| 6,122,341 A | 9/2000 | Butler et al. | 378/20 |

| | | | |
|---|---|---|---|
| 6,135,946 A | 10/2000 | Konen et al. | 600/117 |
| 6,149,592 A | 11/2000 | Yanof et al. | 600/427 |
| 6,165,181 A | 12/2000 | Heilbrun et al. | 606/130 |
| 6,167,145 A | 12/2000 | Foley et al. | 382/128 |
| 6,167,295 A | 12/2000 | Cosman | 600/426 |
| 6,167,296 A | 12/2000 | Shahidi | 600/427 |
| 6,198,794 B1 | 3/2001 | Peshkin et al. | 378/42 |
| 6,203,497 B1 * | 3/2001 | Dekel et al. | 600/439 |
| 6,205,411 B1 | 3/2001 | DiGioia, III et al. | 703/11 |
| 6,216,029 B1 | 4/2001 | Paltieli | 600/427 |
| 6,224,613 B1 | 5/2001 | Hofstetter | 606/130 |
| 6,226,548 B1 | 5/2001 | Foley et al. | 600/426 |
| 6,236,875 B1 | 5/2001 | Bucholz et al. | 600/407 |
| 6,246,898 B1 | 6/2001 | Vesely et al. | 600/424 |
| 6,256,529 B1 | 7/2001 | Holupka et al. | 600/427 |
| 6,259,943 B1 | 7/2001 | Cosman et al. | 600/429 |
| 6,275,725 B1 | 8/2001 | Cosman | 600/426 |
| 6,285,902 B1 | 9/2001 | Kienzle, III et al. | 600/427 |
| 6,298,262 B1 | 10/2001 | Franck et al. | 600/426 |
| 6,332,891 B1 | 12/2001 | Himes | 606/169 |
| 6,341,231 B1 | 1/2002 | Ferre et al. | 600/424 |
| 6,351,659 B1 | 2/2002 | Vilsmeier | 600/407 |
| 6,351,662 B1 | 2/2002 | Franck et al. | 600/429 |
| 2001/0007919 A1 | 7/2001 | Shahidi | 600/427 |
| 2001/0027271 A1 | 10/2001 | Franck et al | 600/426 |
| 2001/0039421 A1 | 11/2001 | Heilbrun et al. | 606/130 |

FOREIGN PATENT DOCUMENTS

| | | |
|---|---|---|
| DE | 297 04 393 U1 | 7/1997 |
| EP | 0 062 941 A1 | 10/1982 |
| EP | 0 326 768 A2 | 8/1989 |
| EP | 0 591 712 A1 | 4/1994 |
| EP | 0 647 428 A2 | 4/1995 |
| EP | 0 832 609 A2 | 4/1998 |
| GB | 2 094 590 A | 9/1982 |
| WO | WO 82/04157 | 11/1982 |
| WO | WO 90/05494 | 5/1990 |
| WO | WO 91/07726 | 5/1991 |
| WO | WO 94/23647 | 10/1994 |
| WO | WO 94/24933 | 11/1994 |
| WO | WO 95/15729 | 6/1995 |
| WO | WO 95/31148 | 11/1995 |
| WO | WO 96/11624 | 4/1996 |
| WO | WO 97/29685 | 8/1997 |
| WO | WO 97/29709 | 8/1997 |
| WO | WO 97/47240 | 12/1997 |
| WO | WO 98/08112 | 2/1998 |

* cited by examiner

METHOD AND DEVICE FOR PERCUTANEOUS DETERMINATION OF POINTS ASSOCIATED WITH THE SURFACE OF AN ORGAN

RELATED APPLICATIONS

The present application is a continuation of application no. PCT/EP99/02634, filed Apr. 20, 1999, which application is incorporated herein in its entirety.

FIELD OF THE INVENTION

The present invention relates to a device and method for percutaneous determination of locations associated with a surface of an organ.

BACKGROUND OF THE INVENTION

Medical imaging is used extensively in orthopaedics to view the state of musculo-skeletal structures that require correction, repair or replacement. Planar X-ray, X-ray computed tomography (CT) and magnetic resonance imaging (MRI) are image modalities used preoperatively to diagnose and plan surgical interventions. Transfer of image data to the surgical theater, however, is still mainly intuitive. Computer assisted surgery (CAS), image guided surgery and medical robotics provide a quantitative link between medical imaging using images acquired preoperatively or intraoperatively and surgical actions allowing the surgeon to view, in real time, the orientation of the surgical instruments relative to the patient. This provides the surgeon with a means to precisely navigate and plan tool movements with respect to normally hidden anatomical structures.

A key issue in computer assisted surgery (CAS) is to establish a relationship between the patient's intraoperative position within an on-site coordinate system and the data of the medical images. The process of computing a transformation from coordinates within an on-site coordinate system to image coordinates is referred to as "registration" or "matching". In the new field of computer assisted surgery (CAS), light-weight "dynamic reference bases" allow the surgeon to freely manipulate the patient during complex procedures without losing valuable image generated data. Registration or matching implies obtaining coordinates of points in the medical image reference frame and in the on-site three-dimensional coordinate system in space from the position measurement device.

Current registration processes are invasive requiring the surgeon to have direct access to fiducial markers implanted in the bone or specific, predetermined landmarks on bone surfaces that are digitized with a positioning device. Recent developments allow the surgeon to obtain a number of points of the bone with the positioning device and this "cloud of points" can be mathematically fit onto the medical image (e.g. Computer tomogram CT) of the bone surface through an optimization algorithm. This process is termed "surface matching." Although these invasive registration processes have greatly improved the versatility of CAS systems, they require large incisions or transcutaneous needles that pierce the skin and touch the surface of the bone. Because orthopaedic surgery often involves bones hidden deep beneath soft tissues, open procedures can expose the patient to both significant risks of infection and long recovery times.

U.S. Pat. No. 5,447,154 to Cinquin, et al. discloses a method for determining the position of an organ and for positioning a therapeutic or diagnostic tool as a function of three-dimensional images. The images can be preoperative images, such as X-ray computed tomography (CT) images or Magnetic Resonance Images (MRI) of a patient's organ. A device provides a sparse set of three-dimensional surface points on the organ of interest during surgery. These surface points are registered (matched) with the three-dimensional functional image, which contains far more detailed information on the organ's surface morphology. Echography probes are used to intra-operatively obtain the sparse set of three-dimensional surface points of the organ. The organ surface is obtained by analyzing a reconstructed two-dimensional "image slice" provided by the ultrasound probe. Both the ultrasound probe and the organ are instrumented with a three-dimensional position tracking device which allows calculation of the identified surface point in 3D space with respect to the patient.

A device for recording ultrasound images is disclosed by WO98/08112 to Emmenegger et al. The position of each ultrasound image is uniquely defined with respect to any arbitrary three-dimensional coordinate system in space through determination of the position and orientation of the ultrasound head. The device comprises an ultrasound head, which can be freely moved by hand, an ultrasound recording apparatus and a three-dimensional position measurement system to determine the position of the ultrasound head. The position of the ultrasound head is determined by measuring lengths of at least three points affixed to the ultrasound head. The length measurements are realized via interchanging electromagnetic energy between markers attached to the ultrasound head and sensors that are part of the position measurement system.

A disadvantage of known methods and devices is the use of reconstructed ultrasound images to intra-operatively identify points on the organ's surface. Identifying points associated with an organ surface from a noisy ultrasound-generated image is difficult. Much information on exact anatomy contour is lost in image reconstruction and conversion to a video signal and digitization of this signal. Because ultrasound systems are generally designed to image soft tissues, they are sensitive to small changes in acoustic impedances. This produces a considerable amount of "noise" in the constructed image and obscures the surface of the bone. Using the video output of these systems further degrades the signal. The picture must then be manually segmented (i.e. finding the surface of the bone), which requires operator input. Once the picture has been segmented, the surface points can be automatically fitted to the coordinate system of the preoperatively acquired CT image. A practical minimally invasive registration would greatly expand the usefulness of CAS technology.

SUMMARY OF THE INVENTION

One embodiment of the present invention relates to a percutaneous-point determination device for percutaneous determination of coordinates of points associated with the surface of an organ of an animal, such as a human. The organ is preferably a bone. Locations of the points are preferably determined within an on-site coordinate system by processing data obtained from a reflection of a focused one-dimensional ultrasound beam from the organ. The associated points are preferably located at or on the surface of the organ, such as a landmark of a bone.

The device can be used to, for example, determine specific anatomical landmarks, such as the spinous process, and left and right superior facet joints, to be used for paired point matching. The device can also be used to determine a cloud of points associated with the organ surface to be used for surface matching a medical image to the organ.

The device includes a processor to process ultrasound data received from the ultrasound device to thereby provide accurate information on anatomical surface location. The ultrasound data are preferably a raw signal. The processing may be performed in real-time.

The ultrasound beam preferably has a sufficiently narrow width to minimize detection of dispersed signals. The coordinates of points can be determined with at least about 0.5 mm axial accuracy and location of the point in the 3-D coordinate system can be determined with an accuracy of less than about 1 mm.

In a preferred embodiment, the percutaneous-point determination device includes an ultrasound device configured to emit an ultrasound beam along an ultrasound beam axis. The ultrasound beam is preferably focused. The ultrasound beam axis preferably has a known orientation, such as a known orientation with respect to the ultrasound device.

The ultrasound device includes at least three preferably non-collinear markers. The markers can include energy emitting, receiving, or reflecting elements. Energy emitting elements include light emitting elements such as, for example, light emitting diodes (LED's) and infrared light emitting diodes (IRED's). Alternative energy emitting elements include, for example, acoustic transmitters and coils configured to establish a magnetic field.

Energy receiving elements include light sensitive elements, such as, for example, photodiodes. Other suitable energy receiving elements include, for example, microphones or Hall-effect elements.

A position measurement device is configured to determine the position of the markers with respect to a three-dimensional reference coordinate system, which may be an on-site coordinate system. The device includes a computer in communication with the ultrasound device and position measurement device. The computer is configured, such as by software, to process ultrasound data received from the ultrasound device and position data received from the position measurement device to thereby determine the location of the point. The ultrasound device is preferably an integral element of a computer assisted surgery system (CAS).

The ultrasound device also comprises a transducer to emit and receive, preferably alternately, acoustic energy such as ultrasonic waves, preferably in the form of an ultrasonic beam. A pulser is configured to cause the transducer to emit the acoustic energy. A receiver receives and preferably amplifies the echo of the ultrasound signal emitted by the transducer. The ultrasound device receiving the echo of the ultrasound signal is configured to output ultrasound data indicative of a distance from the ultrasound device to the point. The pulser and receiver are preferably combined and under computer control. A converter converts the analog signal received from the combined pulser/receiver unit into a digital signal.

The ultrasound device preferably emits the ultrasound beam along an ultrasound beam axis. The one-dimensional acoustic signals can be processed with minimal signal processing thereby increasing measurement speed. A point to be located within the coordinates of a three-dimensional coordinate system is defined by the point of intersection of the ultrasound beam axis and the surface of the organ. Because the location, i.e., position and orientation, of the ultrasound device can be determined by the position measuring device, the location of the point within the coordinate system of the ultrasound probe can be determined using the received acoustic signals. The computer is configured to convert the coordinates of the point from the coordinate system of the ultrasound device into coordinates within the on-site coordinate system, such as relative to the organ or other reference base. Thus, the computer processes the ultrasound data and position data to thereby determine the location of a point associated with the surface of the organ.

In another embodiment, the device is provided with a high-speed analog to digital converter board (ADC), a fast processor and signal analysis software in order to obtain real-time data processing. The transducer is preferably configured to emit acoustic energy having a predetermined frequency f, thereby enabling a desired axial resolution of the ultrasound beam at a particular penetration depth of the emitted acoustic energy. The axial resolution is the minimal distance along the ultrasound beam axis that two distinct echoes can be distinguished from one another. It is dependant on the wavelength $\lambda$ of the ultrasound beam wherein the wavelength $\lambda$ is related to the frequency f by $\lambda=c/f$ wherein c is the average velocity of sound. For example, suitable results for obtaining points on a bone surface are achieved using a frequency f of the transducer within the range of 1 MHZ to 15 MHZ, preferably within the range of 4 MHZ to 6 MHZ.

Higher frequencies f provide better resolution but are attenuated faster in tissue than lower frequencies f. As a result, the mean frequency penetrating the tissue becomes lower as it travels deeper into the tissue. Thus, the highest frequency that will penetrate to a given depth is chosen to yield the best axial resolution.

The lateral resolution varies along the depth of the signal but is preferably less than 1 mm at the −9 dB point. The ultrasound beam can be focused within the near field region given by: $N=D2*f/4c$, wherein D is the diameter of the transducer and N is the length of the near field. With higher frequencies and the larger diameter transducers, the beam can be focused more tightly, yielding better lateral resolution.

The diameter of the transducer depends on the application. For example, a smaller diameter is suitable for shallower depths. In one embodiment, the transducer has a diameter of about 12.7 mm. The ultrasound device is preferably provided with lenses such that the ultrasound beam is focusable in order to increase signal quality and accuracy. The device preferably includes a at least one lens to allow the ultrasound beam to be focussed to a lateral resolution of less than about 1 mm over a depth range of from about 1 mm to 80 mm. In the preferred embodiment, two detachable flat surface axicon lenses are used for focusing the ultrasound beam to depths of 5–30 mm and 25–75 mm, respectively, with a lateral resolution of 1 mm at −9 dB. The lenses attached to the ultrasound device, such as with a screw cap, and are designed to have an optimal interface with the skin, i.e., allowing maximum energy to be transferred to the tissue.

In another embodiment, the device comprises a calibration unit to calibrate the ultrasound head. The calibration unit is configured to receive the ultrasound head in a known position and orientation with respect to a reference portion of the calibration unit. The calibration unit allows the calibration of a coordinate system of markers associated with the ultrasound device with respect to the on-site coordinate system to thereby allow the percutaneous determination of the three dimensional position of the point associated with the surface of the organ from which the ultrasound signal is echoed.

The calibration unit preferably includes markers to allow the position and orientation of the calibration unit to be determined by the position measurement device. Therefore, the position measurement device can determine relative positions and orientations of the ultrasound head and calibration unit. Echoes received from the reference portion can be used to calibrate, for example, an offset between the ultrasound head and the reference portion.

The calibration unit is preferably formed of a material in which the sound velocity is known. A suitable material is plastic, for example, a thermoplastic, such as PLEXIGLASS. The calibration unit includes a receiving location, such as a hole having a diameter to receiver the ultrasound device. For example, the calibration unit may be rectangular or cube shaped with the hole drilled in the center such that the distance from the bottom of the hole to the bottom of the calibration unit is in the range of between about 20 mm to 30 mm. During calibration, the ultrasound device is received by the receiving location. Echoes are received from the interface of the bottom of the calibration unit and the surrounding medium, which is preferably air. These echoes are large and easy to detect. Because the speed of sound within the calibration unit and the distance traveled are known, the echo can be used to calculate an offset from the ultrasound device head to the interface.

The offset is preferably used in subsequent determinations of point locations. For example, echos received during calibration are preferably used to determinate a signal template, i.e., instrument response of the ultrasound pulser/receiver. The signal template is reference ultrasound data that can be used in the determination of the distance from the ultrasound device to the organ. For example, during use, point location determination preferably comprises obtaining the cross-correlation of the signal template with received echos. For example, the location of a bone tissue interface can be determined by cross-correlation of the received echo and the signal template. As alternatives to cross-correlation algorithms, a standard deviation algorithm (STDDEV) or a short time Fourier transform algorithim (STFT) can be used.

In another embodiment of the device according to the invention, a 10 MHZ ultrasound device includes a delay line to allow focusing between 1 mm and 10 mm. The transducer is electrically driven and the electrical signal caused by the echo is received by a pulser/receiver, which is controlled by the computer. The pulser/receiver unit is capable of initiating a pulse having an energy between 80 $\mu J$ and 120 $\mu J$, preferably between 95 $\mu J$ and 105 $\mu J$ and has a maximum gain of approximately 50 dB. The pulser/receiver sends a high voltage pulse with a voltage of between 200 V–400 V to excite the transducer. This pulse is sharp, having a width of less than the inverse of the resonance frequency of the transducer. The receiver amplifies and filters the signal received from the transducer.

A preferred embodiment of the invention operates with a CAS application running on a workstation in a client-server architecture. A computer is configured as an ultrasound server and position data of points associated with the organ are transmitted to the client application through a UDP socket connection to the workstation running position measurement software whenever a request is made. The computer employs a client-server architecture including the computer controlling the ultrasound device and a workstation running position measurement software and CAS application. In another embodiment the device includes a single computer comprising hardware and software configured to operate the ultrasound device, the position measurement device and, preferably, a CAS application.

Another embodiment of the invention relates to a method for the percutaneous determination of coordinates of points associated with the surface of an organ of an animal, such as a human. The organ is preferably a bone. The coordinates are preferably determined within a three-dimensional coordinate system.

The method preferably comprises calibrating the ultrasound head and emitted ultrasound beam axis with respect to a coordinate system fixed with the ultrasound device in order to calculate echo distances. The coordinate system fixed with the ultrasound device is calibrated with respect to the on-site coordinate system in order to determine the three dimensional position of the point on the surface of the organ reflecting the ultrasound signal. The coordinates of points on the surface of the organ are determined with respect to a three-dimensional coordinate system by real-time by raw signal processing.

Yet another embodiment of the invention relates to a device for the percutaneous obtainment of coordinates of points on the surface of a human or other animal organ within a three-dimensional coordinate system. The device comprises an ultrasound device having an axis coinciding with an emitted ultrasound beam axis. The ultrasound device includes at least three energy emitting, receiving or reflecting means serving as markers. A position measurement device is configured to determine the position of the markers with respect to a three-dimensional reference coordinate system in space. At least one computer is operably connected to the ultrasound device and the position measurement device. The computer preferably allows real-time determination of coordinates associated with the surface of the organ, which is preferably a bone. The ultrasound device includes focusing means to focus the ultrasound beam, which is preferably highly focusable to thereby increase signal quality and accuracy.

The focusing means are preferably lenses, such as detachable fluid filled lenses or detachable flat lenses. The ultrasound beam is preferably focusable to 1 mm lateral resolution over a range from 1 mm to 80 mm depth. The ultrasound device preferably emits ultrasound having a predetermined frequency to thereby provide a desired axial resolution of the ultrasound beam at a predetermined depth of penetration of the emitted ultrasound. The frequency of the ultrasound is preferably within the range of 1 MHZ to 15 MHZ.

BRIEF DESCRIPTION OF THE DRAWING

The present invention is discussed below in reference to FIG. 1, which shows an embodiment of a percutaneous-point determination device of the invention.

DETAILED DESCRIPTION OF THE PREFERRED EMBODIMENTS

Figure 1:
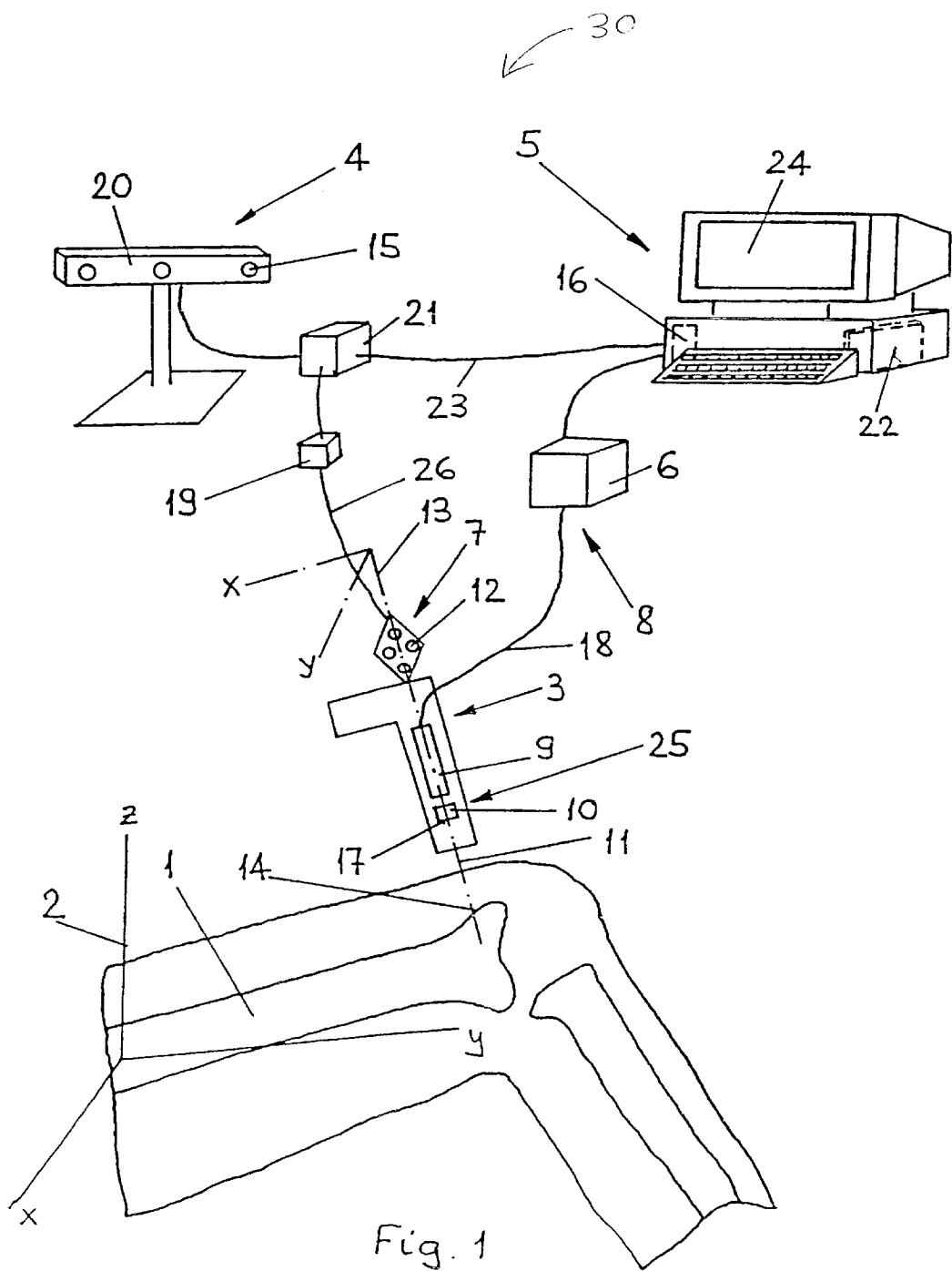

Referring to FIG. 1, a percutaneous-point determination device 30 comprises a three-dimensional position measurement device 4, which is operably connected to a computer 5. An example of a suitable computer is a personal computer comprising a Pentium 166 with MMX. By percutaneous-point determination it is meant that the device is configured to preferably non-invasively determine a location of a point associated with an animal organ, such as a bone of, for example, a human. The point is preferably associated with a surface of the organ, for example, a landmark of the bone. The percutaneous-point determination is preferably effected through the skin or other tissue that covers the organ, preferably without rupturing the skin or tissue.

The percutaneous-point determination preferably comprises directing an ultrasound beam toward the organ and detecting an echo reflected from the organ. The ultrasound beam can pass through tissue before impinging upon the organ. For example, the ultrasound can pass through from about 1 mm to about 80 mm, such as about 5 mm to about 80 mm without undesirably reducing the precision with which the location of the point can be determined.

To provide the ultrasound beam, the percutaneous-point determination device includes a preferably manually and freely moveable ultrasound device 3, which is also operably connected to the computer 5. Ultrasound device 3 includes a transducer configured to emit acoustic energy, preferably in the form of an ultrasonic beam, along an ultrasound beam axis. A longitudinal axis 11 of ultrasound device 3 coincides with the ultrasound beam axis. Transducer 9 receives acoustic energy reflected by an organ, such as a bone 1, along the ultrasound beam axis. During operation, transducer 9 converts voltage into acoustic energy during emission and acoustic energy into voltage during reception.

Ultrasound device 3 is preferably configured to operate in either amplitude mode ultrasound (A-mode) or one-dimensional pulse-echo ultrasound to determine a distance between the ultrasound device head 17 to a point 14 on the surface of the bone 1. Point 14 is defined by the point of intersection between the ultrasound beam axis and the surface of the bone 1 and the ultrasound beam axis. In a preferred embodiment, the ultrasound device 3 operates in one-dimensional pulse-echo ultrasound mode.

To convert the distance between the ultrasound device head 17 and the point 14 on the surface of the bone 1 into coordinates within the on-site three-dimensional coordinate system 2, the position of the ultrasound device head 17 and the direction of the longitudinal axis 11 have to be determined within the on-site three-dimensional coordinate system 2. Therefore, ultrasound device 3 includes markers 12 that allow the position and orientation of ultrasound device 3 to be determined. Markers 12 preferably have a known position and orientation with respect to ultrasound device 3. Preferred markers include electromagnetic energy emitting elements, such as light emitting diodes or infrared light emitting diodes. In a preferred embodiment, device 3 includes four preferably non-collinearly arranged light emitting elements.

Markers 12 establish a three-dimensional coordinate system 13, which has a known relationship with respect to the ultrasound device 3. To determine the position of the ultrasound device head 17 and the orientation of the ultrasound beam axis with respect to the coordinate system 13 of the ultrasound device 3 a calibration is preferably performed, as discussed below. The calibration provides reference ultrasound data indicative of the orientation of the ultrasound beam axis with respect to longitudinal axis 11 and, preferably, the location of ultrasound device head 17 with respect to the coordinate system 13. The reference data can be stored in a electrically erasable programmable read-only memory 19 (EEPROM) attached at the ultrasound device 3 or within a storage medium of computer 5.

The positions of markers 12 are determined with respect to the on-site coordinate system 2 using a position measurement device 4. An example of a suitable position measurement device is the OPTOTRAK model 3020, Northern Digital, Waterloo, Ontario is a suitable position measurement device. Position measurement device 4 preferably comprises a position sensor 20 having at least three light sensitive elements, such as opto-electrical cameras 15. The opto-electrical cameras are preferably charge-coupled devices (CCD) paired with a respective three lens cell and mounted in a stabilized bar. Within each three lens cell, light from an infrared marker is directed onto a CCD and measured. Measurements made by each of the three opto-electrical cameras 15 allow the real-time location of each marker to be determined. Measurement device 4 also includes a system control unit 21, a computer interface card 22, and cables 23, 26.

A point to be located within the coordinates of a three-dimensional coordinate system is defined by the point of intersection of the ultrasound beam axis and the surface of the organ. The ultrasound beam axis preferably has a known orientation with respect to ultrasound device 3. Because the position and orientation of the ultrasound device is known with respect to the markers 12, the orientation of the ultrasound beam axis can be determined by the position measuring device. Once the positions of the markers 12 are determined with respect to the on-site coordinate system 2, the distance between the ultrasound device head 17 and the point 14 on the surface of the bone 1 expressed in coordinates within the coordinate system 13 of the ultrasound device 3 can be converted into coordinates within the on-site coordinate system 2 by means of a coordinate transformation which can be performed via the computer 5. The computer is configured to convert the coordinates of the point from the coordinate system of the ultrasound device into coordinates within the on-site coordinate system, such as relative to the organ or other reference base. A display 24 of computer 5 displays the received ultrasound signal allowing a practitioner to modify equipment parameters, such as the ultrasound frequency, gain, pulse power, pulse energy, and damping to improve bone 1 detection and distance determination.

Ultrasound device 3 includes a pulser/receiver 6, which is controlled by the computer 5 and operably connected to the transducer 9, such as by a coaxial cable 18. Pulser/receiver 6 electrically stimulates transducer 9 to emit acoustic energy. Upon receipt of an echo, pulser/receiver 6 amplifies the voltage signal returned from the transducer 9. The pulser/receiver 6 is configured to initiate a 100 µJ pulse and preferably has a maximum gain of 50 dB. A suitable pulser receiver is a model DPR35-S, Sonix, Inc., Springfield, Va.

The received echo is sampled with a high-speed analog-to-digital conversion (ADC) board at a frequency f, which is preferably at least twice as large as the Nyquist frequency 16. A suitable ADC board is the model STR*864, Sonix, Inc., Springfield, Va. The ADC board is preferably operably connected to the computer 5. The computer is configured, such as by software, to control the pulser/receiver 6 and the ADC board 16.

Pulser/receiver 6 and the ADC board can be operated using a computer program written in a high level language, such as, for example, LabVIEW. The program preferably enables the display of the received ultrasound signal and an adjustment of equipment parameters as gain, pulse power and damping to improve the organ detection and distance evaluation.

Ultrasound head is preferably provided with lens 10, such as detachable flat surface axicon lenses. The lenses preferably allow the ultrasound beam to be focused to from about 5 mm to about 30 mm and from about 25 to about 75 mm. Lenses 10 may be used singly or in combination. A fluid between these lenses 10 and the transducer 9 allows further changes in focus depth to be achieved by varying the fluid density. Water is a preferred fluid.

Received ultrasound signals are processed for viewing in real time 3D data viewing software for viewing in numeric or graphic form. By real time it is meant that the processed signals are available to assist the practitioner in situ, such as during a medical intervention, without causing delays that would impede the medical intervention.

Device 3 preferably comprises a calibration unit to calibrate the ultrasound head. The calibration unit is configured to receive the ultrasound head in a known position and orientation with respect to a reference portion of the calibration unit. The calibration unit preferably includes markers to allow the position and orientation of the calibration unit to be determined by the position measurement device. Therefore, the position measurement device can determine relative positions and orientations of the ultrasound head and calibration unit. Echoes received from the reference portion can be used to calibrate, for example, an offset between the ultrasound head and the reference portion.

The calibration unit is preferably formed of a material in which the sound velocity is known. A suitable material is plastic, for example, a thermoplastic, such as PLEXIGLASS. The calibration unit includes a receiving location, such as a hole having a diameter to receiver the ultrasound device. For example, the calibration unit may be rectangular or cube shaped with the hole drilled in the center such that the distance from the bottom of the hole to the bottom of the calibration unit is in the range of between about 20 mm to 30 mm. During calibration, the ultrasound device is received by the receiving location. Echoes are received from the interface of the bottom of the calibration unit and the surrounding medium, which is preferably air. These echoes are large and easy to detect. Because the speed of sound within the calibration unit and the distance traveled are known, the echo can be used to calculate an offset from the ultrasound device head to the interface.

The offset is preferably used in subsequent determinations of point locations. For example, echos received during calibration are preferably used to determinate a signal template or instrument response of the ultrasound pulser/receiver. During use, point location determination preferably comprises obtaining the cross-correlation of the signal template with received echos. For example, the location of a bone tissue interface can be determined by cross-correlation of the received echo and the signal template. As alternatives to cross-correlation algorithms, a standard deviation algorithm (STDDEV) or a short time Fourier transform algorithim (STFT) can be used.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A percutaneous-point determination device for determining a location of a point associated with a surface of an animal organ, comprising:
    an ultrasound device configured to emit a focused ultrasound beam along an ultrasound beam axis having a known orientation with respect to the ultrasound device, the ultrasound device configured to output ultrasound data indicative of a distance from the ultrasound device to the point associated with the surface of the animal organ, the ultrasound device comprising a plurality of spatial markers having a known spatial relationship to the ultrasound device, the spatial markers configured to radiate energy;
    a position measurement device configured to detect energy radiated by the spatial markers to thereby determine spatial positions of the spatial markers and to output position data indicative of a location of the ultrasound device; and
    a computer configured to process the ultrasound data and position data to thereby determine the location of the point associated with the surface of the animal organ with respect to an on site reference coordinate system.

2. The percutaneous-point determination device of claim 1, wherein the animal organ is a bone of a human.

3. The percutaneous-point determination device of claim 2, wherein the emitted ultrasound beam passes through from about 1 mm to about 80 mm of tissue before impinging upon the bone.

4. The percutaneous-point determination device of claim 2, wherein the emitted ultrasound beam passes through from about 5 mm to about 80 mm of tissue before impinging upon the bone.

5. The percutaneous-point determination device of claim 1, wherein the emitted ultrasound beam has a variable frequency to provide a predetermined axial resolution along the ultrasound beam axis.

6. The percutaneous-point determination device of claim 5, wherein the frequency of the emitted ultrasound beam is variable between about 1 MHZ and about 15 MHZ.

7. The percutaneous-point determination device of claim 1, wherein the emitted ultrasound beam passes through at least one of a fluid filled lens and a flat lens to thereby focus the ultrasound beam.

8. The percutaneous-point determination device of claim 7, wherein the lenses are detachable.

9. The percutaneous-point determination device of claim 1, wherein the ultrasound beam is focusable to a lateral resolution of about 1 mm or less.

10. The percutaneous-point determination device of claim 1, wherein the computer is configured to cross-correlate the ultrasound data with reference ultrasound data to thereby determine the distance from the ultrasound device to the point.

11. A percutaneous-point determination device for determining a location of a point associated with a surface of an animal organ, comprising:
    an ultrasound device configured to emit an ultrasound beam along an ultrasound beam axis having a known orientation with respect to the ultrasound device, the ultrasound device configured to output ultrasound data, the ultrasound device comprising a plurality of spatial markers having a known spatial relationship to the ultrasound device, the spatial markers configured to radiate energy;
    a position measurement device configured to detect energy radiated by the spatial markers to thereby determine spatial positions of the spatial markers and to output position data indicative of a location of the ultrasound device; and
    a computer configured to cross-correlate the ultrasound data with reference ultrasound data indicative of an instrument response of the ultrasound device to thereby provide distance data indicative of a distance from the ultrasound device to the point, wherein the computer is further configured to process the distance data and the position data to thereby determine the location of the point.

12. The percutaneous-point determination device of claim 11, wherein the animal organ is a bone of a human.

13. The percutaneous-point determination device of claim 11, wherein the emitted ultrasound beam passes through from about 1 mm to about 80 mm of tissue before impinging upon the bone.

14. The percutaneous-point determination device of claim 12, wherein the emitted ultrasound beam passes through from about 5 mm to about 80 mm of tissue before impinging upon the bone.

15. The percutaneous-point determination device of claim 14, wherein the emitted ultrasound beam has a variable frequency to provide a predetermined axial resolution along the ultrasound beam axis.

16. The percutaneous-point determination device of claim 15, wherein the frequency of the emitted ultrasound beam is variable between about 1 MHZ and about 15 MHZ.

17. The percutaneous-point determination device of claim 11, wherein the emitted ultrasound beam passes through at least one of a fluid filled lens and a flat lens to thereby focus the ultrasound beam.

18. The percutaneous-point determination device of claim 17, wherein the lenses are detachable.

19. The percutaneous-point determination device of claim 11, wherein the ultrasound beam is focusable to a lateral resolution of about 1 mm or less.

20. A percutaneous method for determining a location of a point associated with a surface of an animal organ, comprising:

providing an ultrasound device emitting a focused ultrasound beam along an ultrasound beam axis having a known orientation;

obtaining ultrasound data indicative of a distance from the ultrasound device to the point associated with a surface of an animal organ;

detecting energy radiated by spatial markers having a known spatial relationship with the ultrasound device to thereby obtain position data indicative of a location of the ultrasound device; and processing the ultrasound data and position data to thereby determine a location of the point associated with a surface of an animal organ with respect to an on-site reference coordinate system.

21. The percutaneous method of claim 20, wherein processing the ultrasound data comprises cross-correlating the ultrasound data with reference ultrasound data.

22. The percutaneous method of claim 20, further comprises focusing the ultrasound beam to provide a focused ultrasound beam having a lateral resolution of about 1 mm or less.

* * * * *